United States Patent [19]
George

[11] Patent Number: 5,611,797
[45] Date of Patent: Mar. 18, 1997

[54] COMBINATION HANDPIECE AND SURGICAL LASER TOOL

[75] Inventor: Virginia C. George, 8164 Capitola Ave., Fair Oaks, Calif. 95628

[73] Assignee: Virginia C. George, Fair Oaks, Calif.

[21] Appl. No.: 507,581

[22] Filed: Jul. 26, 1995

[51] Int. Cl.⁶ .................................................. A61B 17/36
[52] U.S. Cl. ........................................... 606/16; 606/2
[58] Field of Search .................................. 606/14, 15, 16, 606/19, 17, 1

[56] References Cited

U.S. PATENT DOCUMENTS

| | | | |
|---|---|---|---|
| 2,855,679 | 10/1958 | Gibble . | |
| 3,590,232 | 6/1971 | Sadowski | 240/2 |
| 4,459,986 | 7/1984 | Karaki | 606/19 |
| 4,607,622 | 8/1986 | Fritch et al. | 128/6 |
| 4,658,817 | 4/1987 | Hardy | 606/19 |
| 4,782,819 | 11/1988 | Adair | 606/15 |
| 4,785,805 | 11/1988 | Joffe et al. | 606/15 |
| 5,193,526 | 3/1993 | Daikuzon | 606/15 |
| 5,299,560 | 4/1994 | Hatori | 128/4 |
| 5,309,895 | 5/1994 | Yabe | 128/6 |
| 5,411,500 | 5/1995 | Lafferty et al. | 606/15 |
| 5,413,555 | 5/1995 | McMahan | 606/19 |
| 5,441,496 | 8/1995 | Easley et al. | 606/15 |
| 5,474,449 | 12/1995 | Loge et al. | 606/19 |
| 5,478,338 | 12/1995 | Reynard | 606/15 |
| 5,545,153 | 8/1996 | Grinblat et al. | 606/15 |

*Primary Examiner*—Angela D. Sykes
*Assistant Examiner*—Sonya Harris-Ogugua
*Attorney, Agent, or Firm*—Flehr, Hohbach, Test, Albritton & Herbert

[57] ABSTRACT

A combination handpiece and surgical laser tool is disclosed for use in laser surgery. The handpiece comprises a hollow body having an internal wall which is mounted about the probe of the laser tool. A layer which contains optical fibers is mounted about the internal wall with the fibers have outlet ends at the tip of the handpiece. A light source directs visible white light along the fibers with the light being projected in a pattern which illuminates a portion of an anatomical structure in a path about a spot at which the laser beam impinges. In one embodiment a handpiece is releasably fitted about the laser tool so that the handpiece can be detached and used as a flashlight to explore the wound. In another embodiment the optical fibers are formed into discrete clusters which are spaced about the circumference of the annular layer of the handpiece. Visible light can then be projected from the clusters in discrete spots about the laser beam.

19 Claims, 2 Drawing Sheets

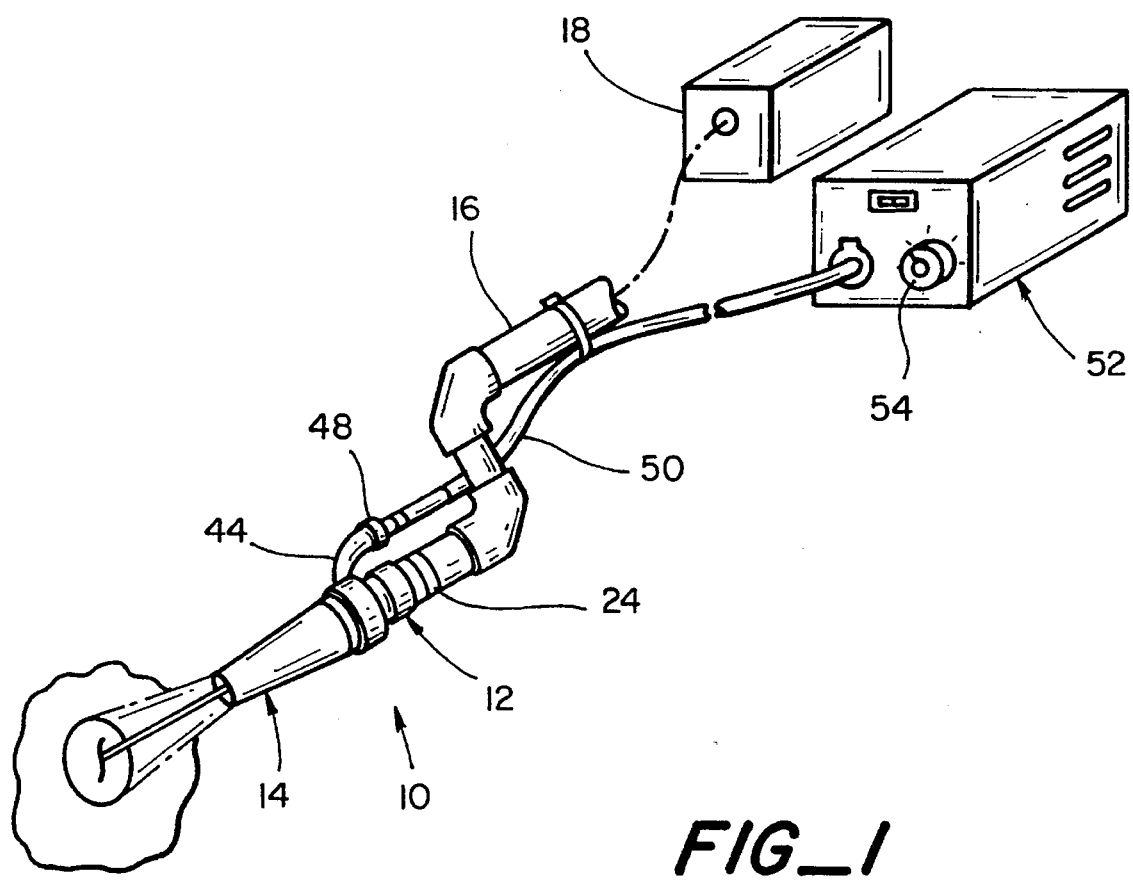
FIG_1
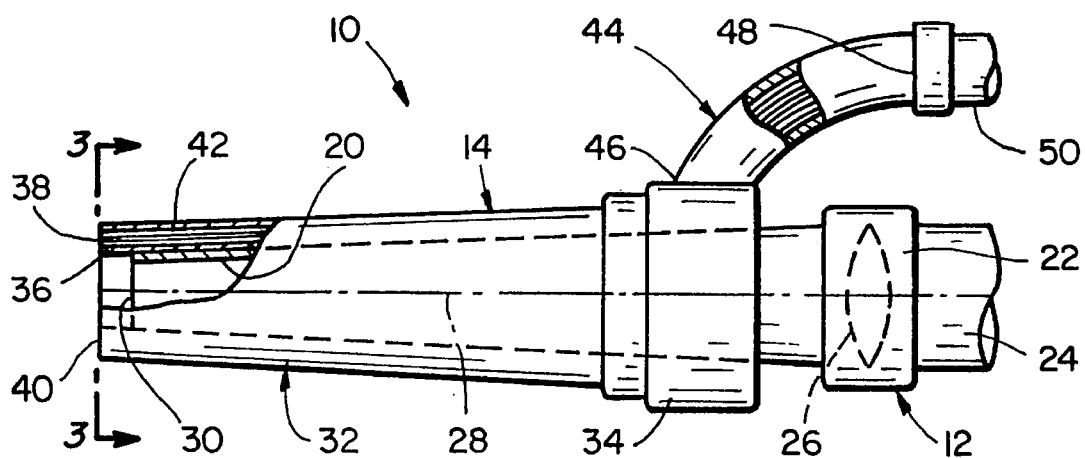
FIG_2

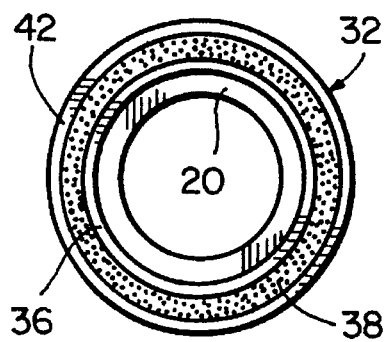
FIG_3
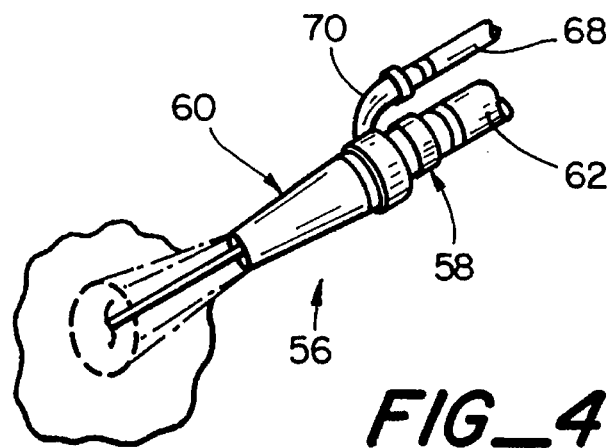
FIG_4
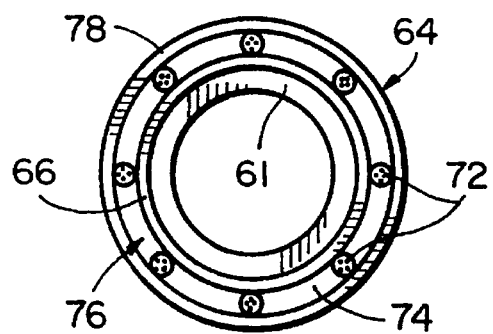
FIG_5

COMBINATION HANDPIECE AND SURGICAL LASER TOOL

BACKGROUND OF THE INVENTION

1. Field of the Invention

This invention relates in general to surgical procedures employing lasers. More particularly, the invention relates to surgical laser tools of the type used in cutting tissue and coagulation. The invention further relates to surgical laser tools for use in surgical procedures such as urology, abdominal surgery, otorhinolaryngology and gynecology.

2. Description of the Related Art

Lasers have been used as "light knives" in surgical procedures. A typical surgical laser tool employs two lasers, one a cutting or burning laser and the other an aiming beam. High-power $CO_2$ or Argon lasers are typically used for cutting and burning, while a red HeNe laser is used for the aiming beam. The HeNe laser is relatively weak and cool, causing no effects on tissue, while providing a red dot which is focused to where the surgical laser will cut or burn. The surgeon can see only the effects of the cutting laser, not the cutting laser itself, and uses the HeNe laser as the aim point.

In a typical prior art surgical laser tool employing a $CO_2$ laser, the beam is delivered through a mirror system located in an articulated counterbalanced arm to a hand-held tool. In the case of an Argon laser, the beam is delivered through optical fibers to the hand-held tool. When the laser energy is focused onto tissue surface, a small volume of tissue is heated so that only this area is cut off. One advantage to this procedure is that small capillaries are coagulated, preventing hemorrhaging resulting from cut blood vessels and providing better healing.

In surgical procedures good lighting for visualization is always important. This is especially true in laser surgery because, unlike a scalpel, the surgeon has no kinesthetic feel or "drag" when moving the laser beam across the anatomical structure. In addition, surgery is often done in dark holes of the wound, which are difficult to illuminate. Most importantly, the HeNe beam is bright red, making it difficult for the surgeon to distinguish between the slightly different shades of red in the wound which denote different structures. After some time with the HeNe beam, a "red out" effect on the surgeon's eyes can occur. The surgeon must then remove the laser from the wound in order to recover color balance and become reoriented to the anatomical structures.

The need has been recognized for a surgical laser tool which obviates the foregoing and other limitations and disadvantages in the prior art. Despite the various surgical laser tools in the prior art, there has heretofore not been provided a suitable and attractive solution to these problems.

OBJECTS AND SUMMARY OF THE INVENTION

It is a general object of the present invention to provide a new and improved handpiece for use with surgical laser tools as well as a new and improved combination handpiece and surgical laser tool.

Another object is to provide a combination handpiece and surgical laser tool which facilitates the surgeon observing and locating the aim point of a laser beam on anatomical structures within a wound, and which obviates the problem of the surgeon getting "red out" from the use of an HeNe laser beam.

Another object is to provide an illuminating handpiece which can be slipped onto an existing surgical laser tool so that the combination projects a ring of shadowless light around the location of the laser beam where the surgery is being performed.

The invention in summary provides a handpiece comprising a hollow tubular body having a tip end from which a pattern of visible white light is emitted. The tubular body surrounds a surgical laser tool which directs a laser beam along an axis within the light pattern. On the anatomical structure the light pattern surrounds the spot at which the laser beam impinges on the structure. In one embodiment the handpiece is releasably mounted on the laser tool so that it can be detached by the surgeon for use in the manner of a flashlight for examining the area of surgery.

The foregoing and additional objects and features of the invention will appear from the following specification in which the several embodiments have been set forth in detail in conjunction with the accompanying drawings.

BRIEF DESCRIPTION OF THE DRAWINGS

FIG. 1 is a partially broken-away perspective view illustrating the combination handpiece and surgical laser tool in accordance with one embodiment of the invention.

FIG 2 is an enlarged side elevational view, partially broken-away, of the handpiece and surgical laser tool shown in FIG. 1.

FIG. 3 is enlarged end view taken along the line 3—3 of FIG. 2.

FIG. 4 is a fragmentary perspective view of a combination handpiece and surgical laser tool in accordance with another embodiment.

FIG. 5 is an enlarged end view of the handpiece and tool shown in FIG. 4.

DESCRIPTION OF THE PREFERRED EMBODIMENTS

In the drawings FIGS. 1–3 illustrate a combination handpiece and surgical laser tool 10 in accordance with one embodiment of the invention. The combination handpiece and laser tool is comprised of a tapered hollow probe 12 and illuminating handpiece 14. The probe is mounted on the end of an articulated arm 16 having a conventional counterbalance, not shown, which permits the surgeon to move and aim the tool with minimal effort. The articulated arm is hollow and contains a conventional system of mirrors, not shown, which receives and directs a beam of invisible $CO_2$ cutting laser, and a red HeNe laser aiming beam, from a suitable laser generating unit 18.

Probe 12 is comprised of a frusto-conical outer wall 20, preferably of aluminum, which is mounted at its proximal end to a collar 22. The collar in turn is detachably mounted by means of coupling 24 to the outlet end of the articulated arm. A focusing mirror 26 mounted within the proximal end of the probe focuses the $CO_2$ and HeNe laser beams along the longitudinal axis 28 of the probe and out through the probe's distal end 30. The lens focuses the beams to a point or spot at a short distance, on the order of 3", from the outer end of the laser tool.

Illuminating handpiece 14, in the embodiment of FIGS. 1–3, is detachably mounted to the probe. The handpiece is comprised of a hollow tubular body 32 which is mounted at its proximal end by a suitable means such as welding to a collar 34. The tubular body and collar preferably are of aluminum metal for purposes of saving weight.

Tubular body 32 is comprised of a frusto-conical internal wall 36 which is sized and shaped commensurate with the outer wall of the probe so that the handpiece can be slipped over and form a releasable friction fit with the surface of the probe. The end piece further comprises an annular layer 38 of closely packed optical fibers which extend in parallel relationship along the length of internal wall 36. The diameters of the optical fibers are threadlike in size. The outer ends of the fibers terminate at tip end 40 of the handpiece. An outer cover 42 of a suitable material such as aluminum is mounted about annular layer 38 to contain and protect the optical fibers.

A goose-necked shaped tubular extension 44 is secured as by welding to an opening 46 on one side of the handpiece collar. A coupling 48 connects the goose-neck extension with a flexible tube 50 which extends to a light source 52. The optical fibers extend continuously from the outlet of the light source through transfer portions of the fibers contained in tube 50, into goose-neck extension 44 and along annular layer 38. Within collar 34 the optical fibers are distributed in paths so that they form an annular array in layer 38. Tube 50 with its bundle of optical fibers is sufficiently flexible so that it can easily bend as the articulated arm is moved when the laser tool is repositioned by the surgeon. A suitable control 54 is provided on the light source for selectively adjusting the intensity of light directed through the optical fibers. The visible light emitted by the source preferably is white light, which is optimum in the invention for use in combination with the red beam of the HeNe laser.

In the use and operation of the invention, handpiece 14 is first slipped over and into a friction fit with probe 12 of the laser tool. Laser source 18 is turned on for emitting the invisible $CO_2$ laser cutting beam and visible red HeNe aiming beam, which are directed along the length of articulated arm 16. The two lasers beams are directed through lens 26 which focuses the beams to a point or spot beyond tip end 40. Light source 52 is then turned on to emit white light which is directed through the bundle of optical fibers which extend continuously through tube 50, goose-neck extension 44 and annular layer 38 of the handpiece. The white light is emitted from the outlet ends of the fibers in a pattern which illuminates the anatomical structure in a path which circumscribes the spot at which the laser beams impinge. This provides a ring of shadowless white light exactly where the surgery is being performed. The red HeNe beam is still visible, but it no longer destroys the surgeon's color balance. While FIG. 1 illustrates the white light as being projected in an outwardly flaring conical pattern, the pattern could be cylindrical.

As required, the surgeon can slip off and detach handpiece 14 from the probe of the laser tool while the light is still being emitted. The handpiece can then be used in the manner of a flashlight for exploring the wound at areas apart from the spot at which the laser beams impinge.

With the invention the surgeon both can see better when actually cutting with the laser and when using the handpiece to explore the wound. The surgeon also becomes less fatigued when using the invention during surgery.

The materials used in fabricating handpiece permit it to be autoclaved for use in sterile procedures.

While in the embodiment of FIGS. 1–3 the pattern of visible light is shown as circular in cross section, other cross sectional shapes could be used by employed appropriately shaped cross sections for annular layer 38, such as oval or polygonal.

FIGS. 4 and 5 illustrate another embodiment providing a combination illuminating handpiece and surgical laser tool 56 which is comprised of a tapered hollow probe 58 and illuminating handpiece 60. Probe 58 is constructed similar to that described for the embodiment of FIGS. 1–3 and includes a tapered outer wall 61. The probe is coupled with the end of an articulated arm 62 which extends from a laser source, not shown, that emits the cutting and aiming laser beams in the manner described above. Illuminating handpiece 60 is releasably fitted over the probe end of laser tool in the manner explained in connection with the embodiment of FIGS. 1–3. Handpiece 60 is comprised of a tubular body 64 having an internal wall 66 which fits about outer wall 61 of the probe.

A plurality of optical fibers are directed from a visible light source, not shown, through a flexible tube 68 and into a goose-neck extension 70 which connects with the proximal end of the handpiece. From the goose-neck extension the optical fibers are distributed to a plurality, shown as eight, of discrete clusters or bundles 72 (FIG. 5) which are circumferentially spaced about the outside of internal wall 66. A filler 74 of a suitable rigid material such as synthetic polymer or resin is molded between the optical fiber bundles to hold them in place. The filler and bundles form an annular layer 76 about which a cover 78 of aluminum is mounted.

Combination handpiece and laser tool 56 is operated in the manner explained in connection with FIGS. 1–3. The optical fiber bundles 72 emit discrete beams of visible white light in a pattern which illuminates the anatomical structure so that the light circumscribes the spot at which the laser beams from the tool impinge. While in this embodiment eight bundles of optical fibers are shown in equally spaced relationship about the circumference of the layer, the invention contemplates that a greater or lesser number of clusters could be provided. Also the light pattern could be of other cross sectional shapes such as oval or polygonal, and the pattern could be either cylindrical or conical.

While the foregoing embodiments are at present considered to be preferred it is understood that numerous variations and modifications may be made therein by those skilled in the art and it is intended to cover in the appended claims all such variations and modifications as fall within the true spirit and scope of the invention.

What is claimed is:

1. A illuminating handpiece for use with a surgical laser tool which includes a probe having an outer wall and an internal passage through which a visible laser beam is focused in a direction from a distal end of the probe toward an anatomical structure, the illuminating handpiece comprising the combination of a hollow body having an internal wall mounted about the outer wall of the probe with the body having a tip end which is positioned about the distal end of the probe; and illumination means carried by the body for directing visible light out from said tip end in a light pattern about a longitudinal axis along which the laser beam extends whereby the visible light illuminates a portion of said anatomical structure in a path which circumscribes a spot at which the laser beam impinges on the anatomical structure.

2. A handpiece as in claim 1 in which said illumination means includes a plurality of optical fibers arrayed in parallel relationship about said internal wall, said optical fibers having outlet ends positioned adjacent said tip end of the body, and means for directing the visible light into and along the optical fibers for projection through said outlet ends and out from the tip end of the body into said light pattern.

3. A handpiece as in claim 2 in which the optical fibers include transfer portions which are external of the body; and means for constraining said transfer portions of the optical fibers in parallel relationship in a flexible bundle whereby a user can move the handpiece and surgical laser tool relative to the anatomical structure while enabling flexure of the bundle.

4. A handpiece as in claim 2 in which portions of the optical fibers adjacent the outlet ends are substantially evenly distributed circumferentially about the internal wall whereby the visible light is projected uniformly along said path of illumination of the anatomical structure.

5. A handpiece as in claim 2 in which the outlet ends of the optical fibers are distributed in a plurality of discrete clusters which are circumferentially spaced about the internal wall whereby the visible light is formed in discrete spots along said path of illumination of the anatomical structure.

6. A handpiece as in claim 2 in which the optical fibers are in an annular wall disposed about the internal layer of the body.

7. A handpiece as in claim 1 in which said illumination means provides an light pattern which is annular.

8. A handpiece as in claim 7 in which said illumination means provides a light pattern which is coaxial with said longitudinal axis of the laser beam.

9. A handpiece as in claim 1 in which said internal wall is frusto-conical shaped, and said outer wall of the probe has a frusto-conical shape commensurate with said shape of the inner wall on the outer wall of the probe where by the body can be releasably detached from the probe for use in projecting the light pattern to a selected area of the anatomical structure apart from the spot at which the laser beam impinges on the anatomical structure.

10. A combination handpiece and surgical laser tool for performing surgery on an anatomical structure with a visible laser beam from a source of laser beam emission, the tool comprising a probe having an internal passage which is elongated along a longitudinal axis, the probe having a distal end and a proximal end with the proximal end being adapted for optical connection with a laser beam emitted from said source; means for directing said laser beam from the source into the proximal end of the probe and along the longitudinal axis of the internal passage, said laser beam being projected out through the distal end of the probe toward the anatomical structure; and a light projector carried by the probe for directing visible light in a light pattern in the direction of and about the laser beam whereby the visible light illuminates a portion of said anatomical structure in an illumination path about a spot at which the laser beam impinges on the anatomical structure.

11. A combination handpiece and surgical laser tool as in claim 10 in which said light projector includes a plurality of optical fibers arrayed in parallel relationship, said optical fibers having outlet ends positioned adjacent the distal end of the probe, and means for directing the visible light into and along the optical fibers for projecting through said outlet ends and toward the anatomical structure.

12. A combination handpiece and surgical laser tool as in claim 11 which further comprises a source of visible light; the optical fibers include transfer portions which are external of the probe with the transfer portions being adapted for optical coupling with the source of visible light; and means for constraining said transfer portions of the optical fibers in parallel relationship in a flexible bundle whereby a user can move the handpiece and surgical laser tool relative to the anatomical structure while enabling flexure of the bundle.

13. A combination handpiece and surgical laser tool as in claim 11 in which portions of the optical fibers adjacent the outlet ends are substantially evenly distributed circumferentially about the distal end whereby the visible light is projected uniformly along said path of illumination of the anatomical structure.

14. A combination handpiece and surgical laser tool as in claim 11 in which the outlet ends are distributed in a plurality of discrete clusters which are circumferentially spaced about the distal end whereby the visible light is projected in discrete spots along said illumination path.

15. A combination handpiece and surgical laser tool as in claim 11 in which the optical fibers are in an annular layer disposed about the distal end of the probe.

16. A combination handpiece and surgical laser tool as in claim 10 in which said illumination means provides a light pattern which is annular.

17. A combination handpiece and surgical laser tool as in claim 16 in which said illumination means provides a light pattern which is coaxial with said longitudinal axis of the laser beam.

18. A combination handpiece and surgical laser tool as in claim 10 in which said illumination means provides a emitted laser beam which is red and the visible light which is white.

19. A combination handpiece and surgical laser tool as in claim 10 including means for releasably mounting the light projector on the probe whereby the light projector can be detached from the probe for use in projecting the light pattern to a selected area of the anatomical structure apart from the spot at which the laser beam impinges.

* * * * *